United States Patent [19]

Tachibana et al.

[11] Patent Number: 4,481,138

[45] Date of Patent: Nov. 6, 1984

[54] HEPTADECAPEPTIDE

[75] Inventors: Shinro Tachibana; Kengo Araki, both of Kashiwa; Shizuko Ohya, Ushikumachi; Seiji Yoshida, Urayasu, all of Japan

[73] Assignee: Eisai Co., Ltd., Tokyo, Japan

[21] Appl. No.: 400,324

[22] Filed: Jul. 21, 1982

[30] Foreign Application Priority Data

Jul. 21, 1981 [JP] Japan .............................. 56-112950

[51] Int. Cl.³ ........................................... C07C 103/52
[52] U.S. Cl. ............................................. 260/112.5 R
[58] Field of Search ................... 424/177; 260/112.5 R

[56] References Cited

U.S. PATENT DOCUMENTS

| | | | |
|---|---|---|---|
| 3,013,944 | 12/1961 | Jorpes et al. | 260/112.5 R |
| 4,117,117 | 9/1978 | Wunsch | 260/112.5 R |
| 4,172,130 | 10/1979 | Kisfaludy et al. | 260/112.5 R |

OTHER PUBLICATIONS

Beaumont and Hughes, *Biology of Opioid Peptides*, Ann. Rev. Pharmacol. Toxicol. 1979, 19:245–267.
*The Merck Index*, Ninth Edition, 1976, pp. 283 and 1091.
Chikara Oyama: Shindan to Chiryo (Diagnosis and Therapy) 68, pp. 825–827 (1980).
Tampakushitsu, Kakusan, Koso (Protein, Nucleic Acid and Enzyme), vol. 26, No. 2, pp. 1–36 (1981).
Suzuki, Araki and Tachibana: Yakugaku-Zasshi 99, pp. 172–179 (1979).

*Primary Examiner*—Delbert R. Phillips
*Assistant Examiner*—F. T. Moezie
*Attorney, Agent, or Firm*—Flynn, Thiel, Boutell & Tanis

[57] ABSTRACT

A substance having opiate and analgesic activity is obtained from swine duodenum. The opioid substance of the present invention comprises a heptadecapeptide having the following primary amino acid structure: Tyr-Gly-Gly-Phe-Leu-Arg-Arg-Ile-Arg-Pro-Lys-Leu-Lys-Trp-Asp-Asn-Gln.

1 Claim, 5 Drawing Figures

HEPTADECAPEPTIDE

This invention relates to a novel heptadecapeptide having an analgesic activity and, more particularly, to a heptadecapeptide having opiate activity contained in a vasoactive intestinal peptide (hereinafter referred to as VIP) fraction obtained from a swine duodenum.

The inventors of this invention have long studied extraction of gastrointestinal hormones such as secretin, cholecystokinin pancreozymin and vasoactive intestinal peptides from a source material of swine duodena and their use, and have unexpectedly found that a substance having an opiate activity is contained in the VIP fraction. We have, therefore, made further extraction, purification and analysis of said substance and found that said substance is a peptide represented by a novel primary structure having an opioid activity several hundred times stronger than morphine. Thus, we have achieved this invention.

Enkephalin and endorphin occur in the brain as endogeneous opioid substances, and these substances are thought to control various body senses including the sense of pain and mental actions. Enkephalin includes two types of pentapeptides, that is, methionine enkephalin and leucine enkephalin, and these two peptides are thought to have different physiological actions. It is also known that endorphin has molecular heterogeneity, that is, $\alpha$, $\beta$, $\gamma$, or $\delta$-endorphin forms exist, and $\beta$-endorphin consisting of 31 amino acids has the strongest analgesic action. The following references describe general knowledge on endorphins: A. Beaumont, J. Hughes: Ann. Rev. Pharmacol. Toxicol. 19, 245 (1979); Chikara Oyama: Shindan to Chiryo (Diagnosis and Therapy) 68, 825 (1980); Tampakushitsu, Kakusan, Koso (Proteins, Nucleic acids, and Enzymes) Vol. 26, No. 2 (1981), special vol. on opioid peptides.

Recently, it was suggested that endogeneous opiate substances are contained not only in the brain but also in other parts of the body and, in fact, a few peptides which are thought to be enkephalin precursors have been separated from adrenal medulla. The presence of opioid substances in the intestinal tract has also heretofore been indicated by immunological techniques such as immuno histochemistry, radioimmunoassay and an in vitro bioassay.

However, details are not known concerning methods of their extraction and purification, structures, pharmacological activities and the like.

The substance which is provided in this invention by the inventors is an extract from the intestinal tract which is not known in detail. It has become clear that the substance is different from the aforementioned known endogeneous opioid substances such as enkephalin or endorphin and that it has an opiate activity stronger than that expected from previous knowledge. Accordingly, this invention represents a distinct advance.

This invention will be described below in further detail.

The substance of this invention is a heptadecapeptide having a primary structure:

Tyr—Gly—Gly—Phe—Leu—Arg—Arg—Ile—Arg—Pro—Lys—Leu Lys—Trp—Asp—Asn—Gln, wherein Asp represents aspartic acid, Asn represents asparagine and Gln represents glutamine.

This primary structure is determined by analyses as set forth in the Example below, i.e., analysis of amino acid composition and identification by means of dansylation of N-terminal amino acid of the substance of this invention; analysis of amino acid composition, identification of N-terminal amino acid and amino acid sequence by Edman degradation about the fragments obtained by trypsin hydrolysis of the substance of this invention: and the determination of changes in quantities of amino acids released by carboxypeptidase hydrolysis of the substance of this invention with time.

The substance of this invention can be extracted from a swine duodenum. Its extraction and purification can be conducted according to a conventional method, and the following summarized method is shown as an example. In the first step, VIP fractions are prepared from swine duodena according to a method, for example, described in Yakukaku-Zasshi vol. 99, p. 172 (1979) by Suzuki, Araki and Tachibana. Next, the VIP fractions are concentrated by purification techniques including CM-cellulose column chromatography, Sephadex G 25 gel filtration and CM-Sephadex column cromatography. Here, the determination of an active fraction is carried out by a bioassay using longitudinal muscle preparations of guinea pig ileum (technique set forth in Item (2) Method in the Test Example below). Next, the active fraction is collected, salted out and subjected again to gel filtration using Bio Gel P 6. This gel filtration is preferably carried out first under a weakly alkaline condition and, then, under a weakly acidic condition, thereby increasing the relative activity markedly. Then, the active fraction is freeze-dried and subjected to a reversed phase high performance liquid chromatography using Nucleosil C 18. An aqueous acetonitrile solution containing trifluoroacetic acid is used as the developing solvent, and an acetonitrile concentration gradient from 10 to 40% is preferred. The single peptide of this invention is obtained by repeating freeze drying and reversed phase high speed liquid chromatography and finally subjecting the fraction to the reversed phase high performance liquid chromatography using a Nucleosil Phenyl.

The utility of the substance of this invention as an analgesic substance is proved by the following test example.

TEST EXAMPLE

(1) Sample

The substance of this invention prepared according to the method set forth in the Preparation Example was used as a test sample. Morphine was used as a control sample.

(2) Method

The following two methods (A) and (B) set forth below were used.

(A) Testing Method using a longitudinal muscle preparation of guinea pig ileum

The technique by H. W. Kosterlitz et al. was applied. That is, an adult guinea pig was exsanguinated by cutting the jugular vein and, immediately after laparotomy, the ileum, 40 to 50 cm-long section, was cut off at a point 15 to 20 cm distant from the ileocecal region, immediately placed in a Ringer's solution, and cut into 10-cm segments. Longitudinal muscles were peeled off from the segments with a surgical knife and an applicator. These muscles were bound with threads to form a ring and placed in a 6-cm constant-temperature glass cell and suspended therein vertically. From platinum electrodes placed at the bottom and the top, an electric stimulus of 0.1 Hz, 0.5 ms and 80–90 volt was applied, and the resulting contraction was recorded via a transducer. When the sample was placed in the cell, the degree of contraction was controlled in reply to the amount of the sample used. This control of contraction was utilized for the determination of opiate activities.

The following is a literature on this method. H. W. Kosterlitz, A. A. Waterfield: Annu. Rev. Pharmacol. 15, 29 (1975)

(B) Technique using mouse vas deferens

The technique by Hughes et al. was applied. That is, an adult male mouse was exsanguinated by decapitation and, immediately after laparotomy, the vasa deferentia were removed. The sperm filled in the vas deferens was squeezed out with tweezers, and both ends of the left and right vas deferens were bound with threads to form a ring. This ring was placed in an electrostimulating apparatus similar to that used in (A) and electrically stimulated under the condition of 0.1 Hz, 1 ms and 90 volt. As was the case with the longitudinal muscle of guinea pig ileum, the contraction by an electric stimulus was controlled to an extent corresponding to the quantity of sample used. This control of contraction was used to determine the opiate activity.

The following is a literature on this technique. H. W. Hughes, H. W. Kosterlitz, F. M. Leslie, Br. J. Pharmacol. 53, 371 (1975).

The potency of opiate activity titer can be expressed in terms of $IC_{50}$ (nMol) which is a concentration necessary to reduce the contraction by electric stimulus to 50% level and hence $IC_{50}$ was determined also in methods (A) and (B).

(3) Results

Table 1 shows the results.

TABLE 1

| Method Sample | (A) | (B) |
|---|---|---|
| Morphine | 105–25 (15) | 220–40 (9) |
| Substance of this invention | 0.55–0.15 (6) | 6.6–2.4 (6) |

In Table 1, the values represent $IC_{50}$ (nMol) and the numerals in the parentheses represent the number of samples.

Table 1 shows that the substance of this invention inhibits the contraction of the longitudinal muscle of guinea pig ileum induced by an electric stimulus, its potency being about 150 times that of morphine, and that the substance of this invention inhibits the contraction of mouse vasa deferentia induced by an electric stimulus, its potency being about 30 times that of morphine.

This invention will be described below with reference to an example.

PREPARATION EXAMPLE

VIP fraction (1 kg) obtained from swine duodena (from twenty-thousand pigs) was passed through a CM-cellulose column (30 cm across, 70 cm long), washed sufficiently (4 l/hr) with a 20-mM phosphate buffer solution and eluted with a sodium phosphate buffer solution having a linear concentration gradient from 20 mM, pH 10 (140 l) to 100 mM, pH 12 (140 l). The active fractions were collected while continuing the analysis by a bioassay set forth in Method (A) in the aforementioned test example.

FIG. 1 is a graph showing the chromatographic profile, wherein closed triangles represent morphine equivalence and closed circles represent protein contents determined by $OD_{280}$ nm. Next, the active fraction was salted out by saturation with salt and, after division into two portions, desalted by passing through a Sephadex G 25 column (21.5 cm × 81 cm) and freeze-dried (78 g).

Next, the active fraction was passed through a CM-Sephadex column (3.5 cm × 90 cm) previously bufferized sufficiently with a 20 mM, pH 10, phosphate buffer solution, washed with the same buffer solution and eluted (107 ml/hr, 15 g/fraction) with a sodium phosphate buffer solution having a linear concentration gradient from 20 mM, pH 10 (3 l) to 100 mM, pH 12, (3 l). While following the activity change by the aforementioned bioassay, the active fraction was collected and salted out with salt (20 g). The salted out fraction was divided into four portions and each portion was passed through a Bio Gel P 6 column (3 cm × 100 cm). First, the fraction was eluted with a 100 mM ammonium bicarbonate solution, and the active fraction was freeze-dried and, then, similarly passed through a Bio Gel P 6 column (2.4 cm × 87 cm) with a 100 mM acetic acid solution. With the 100 mM ammonium carbonate solution, the active fraction was eluted having its peak overlapping that of salt, whereas with the 100 mM acetic acid solution, the active fraction was eluted separately after the peak of salt. FIG. 2 is a graph showing the elution profile obtained by fractionation using a Bio Gel P 6 column and a 100 mM-ammonium bicarbonate nate, wherein the dotted line represents activities in terms of morphine equivalence, and the solid line represents protein contents in terms of $OD_{280}$ nm. FIG. 3 is a graph showing the elution profile obtained by fractionation using a Bio Gel P 6 column and a 100 mM acetic acid solution, wherein the dotted line represents peptide contents in terms of $OD_{225}$ nm and the solid line represents peptide contents expressed in terms of $OD_{280}$ nm. The hatched portion shows the active portion.

The separated active fraction was freeze-dried and dissolved in 1 ml of a solution prepared by mixing an acetonitrile/water mixture (1:9) with 0.065% v/v of trifluoroacetic acid and subjected to reversed phase high performance liquid chromatography using a Nucleosil C 18 column (4.6 mm × 500 mm). Here, the solvent system was a solution prepared by mixing an acetonitrile/water mixture with 0.065% v/v trifluoroacetic acid. This solution had an acetonitrile concentration gradient from 20% to 40% and was passed at a rate of 2 ml/min.

FIG. 4 is a graph showing the result of this chromatography, wherein the dotted line represents the concentration change of acetonitrile and the hatched portion represents an active portion. As shown in FIG. 4, the active fraction was concentrated and leached out near the fraction corresponding to an acetonitrile concentration of 30%. The fraction was freeze-dried, subjected to high performance liquid chromatography using the same conditions and finally subjected to reversed phase high performance liquid chromatography using a Nucleosil Phenyl column (4.6 mm × 250 mm). Here, the developing solvent was a solution prepared by mixing a 30% aqueous acetonitrile solution with 0.065% v/v of trifluoroacetic acid and this solution was passed at a rate of 1 ml/min. The active portion corresponded to optical absorption peaks at 280 nm and 225 nm and was eluted symmetrically.

FIG. 5 is a graph showing the result of this chromatography. The substance produced was converted into a corresponding dansylated derivative by a usual method to confirm its purity. The yield was 15 nmol. The structure of the obtained substance was determined by the analyses set forth in (1) to (4).

(1) Amino acid composition

The peptide (2 nmol) was hydrolyzed at 110° C. for 24 hr in 20 μl of a 3 N-mercaptoethanesulfonic acid and analyzed for its constituent amino acids by a Hitachi Model-835 amino acid analyzer. As a result, it was found that the peptide consisted of 17 amino acids, i.e., 2 Asp, 1 Glu, 2 Gly, 1 Pro, 1 Ileu, 2 Leu, 1 Phe, 1 Tyr, 2 Lys, 3 Arg and 1 Trp.

(2) Identification of N-terminal amino acids

The peptide (1 nmol) was dissolved in 50 μl of a 0.5 N-sodium bicarbonate solution, mixed with 50 μl of an acetone solution containing 1 mg/ml of dansyl chloride and left standing overnight. The dansylated peptide was developed by silica gel thin layer chromatography (TLC), n-BuOH;AcOH:H$_2$O=4:1:5. The spot of the dansylated peptide (R$_f$ 0.3–0.4) was scraped off and eluted with a mixture of MeOH, AcOH, pyridine and H$_2$O (1:1:1:1). After being concentrated and evaporated to dryness in a hydrolysis tube, the peptide was hydrolyzed with 100 μl of 6 N-hydrochloric acid at 105° C. for 16 hr. After distilling off the hydrochloric acid, the hydrolyzate was extracted with 100 μl of water-saturated ethyl acetate. The insoluble matter was centrifuged and the supernatant liquid was analyzed by a HPLC (Waters) Nucleosil C 18 column (4.6 mm×250 mm). As a result, ⊖-DNS-lysine and O,N-diDNS-tyrosine were identified. Accordingly, the N-terminal was estimated as tyrosine (3) Confirmation of the structure of trypsin hydrolyzate The peptide (5 nmol) was dissolved in 100 μl of distilled water. To the solution was added 10 μg/ml of trypsin (Sigma Co.) and 15 μl of a 0.1M-phosphate buffer solution, pH 7.6, and the resulting solution was subjected to enzymatic hydrolysis at 37° C. for 1.5 hr. The hydrolyzate, as such, was subjected to separation treatment using a HPLC (Waters) apparatus under a condition including a Nucleosil C 18 column (4.6 mm×250 mm) and a 0.065% aqueous TFA solution having an acetonitrile concentration increasing linearly from 10 to 60%, to obtain five fragments. Each fragment was tested for amino acid analyses, identification of N-terminal amino acids and determination of amino acid sequence by Edman degradation. As a result, the fragments were estimated to have the following amino acid sequences:

Frag. I; Ile—Arg—Pro—Lys
Frag. II; Arg—Ile—Arg—Pro—Lys
Frag. III; Leu—Lys—Trp—Asp (Asx Glx)
Frag. Iv; Tyr—Gly—Gly—Phe—Leu—Arg—Arg
Frag. V; Tyr—Gly—Gly—Phe—Leu—Arg.

The structures of Fragments I, II, IV and V were confirmed by identifying them with their synthetic standard samples. Here, the following literature is cited for the Edman degradation. Methods in Enzymology Vol. XLVII, Part E, p. 335, Edited by C. H. W. Hrs and S. N. Timasheff, 1977, Academic Press, New York.

(4) Determination of the sequence of C-terminal amino acids

The peptide (1 nmol) together with 1 μg of carboxypeptidase A (Sigma Co.) was incubated in 150 μl of a 0.1M-ammonium acetate buffer solution, pH 8.0, at 33° C. to degrade the peptide. After 2 hr and 16 hr, 50 μl-samples were taken and analyzed for released amino acids by a Hitachi Model-835 amino acid analyzer using a biological fluid column. To the remaining (50 μl) solution was added 1 μg of carboxypeptidase to complete degradation and the solution was hydrolyzed further for 24 hr. After 24 hr, the entire solution was injected in an amino acid analyzer and the free amino acids were quantitatively determined. As a result, it was estimated that the C-terminal was Gln and the penultimate amino acid was were Asp or Asn, that is, the C-terminal part was estimated to be —Asp—Asn—Gln or —Asn—Asp—Gln. On the other hand, from the results of Edman degradation of the trypsin-hydrolyzed fragment III, the third amino acid from the C-terminal was estimated to be Asp. Accordingly, the amino acid sequence of the C-terminal part was determined to be —Asp—Asn—Gln.

From the results of the analyses (1) to (4), the amino acid sequence of the peptide was confirmed to be as follows:

Tyr—Gly—Gly—Phe—Leu—Arg—Arg—Ile—Arg—Pro—Lys Leu—Lys—Trp—Asp—Asn—Gln.

Figure 1:
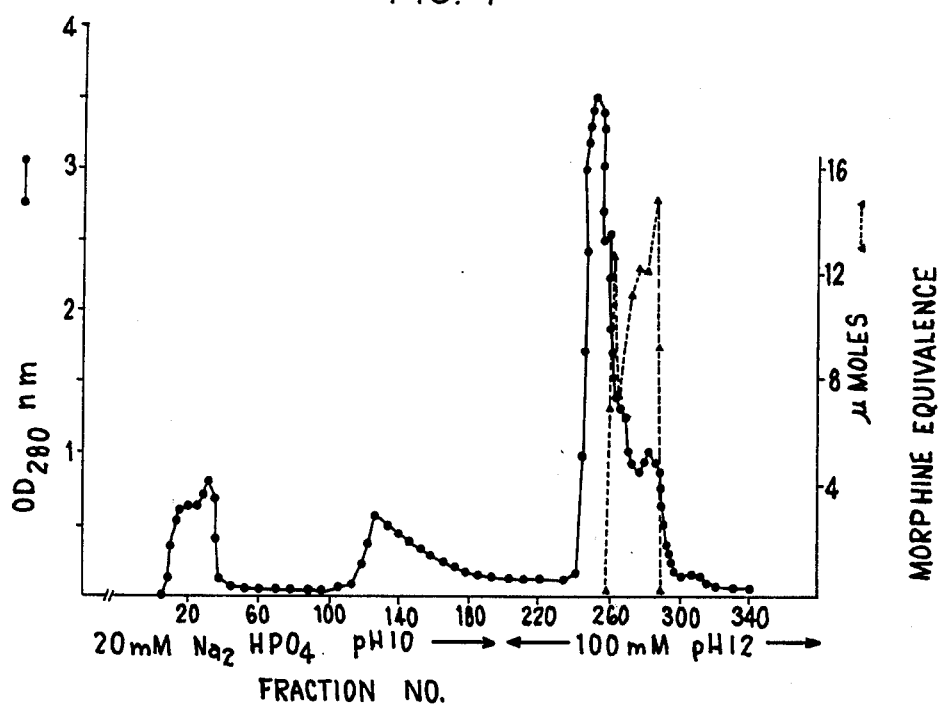
FIG. 1 refers to the Preparation Example and is a graph showing an elution profile obtained by using a CM-cellulose column.
Figure 2:
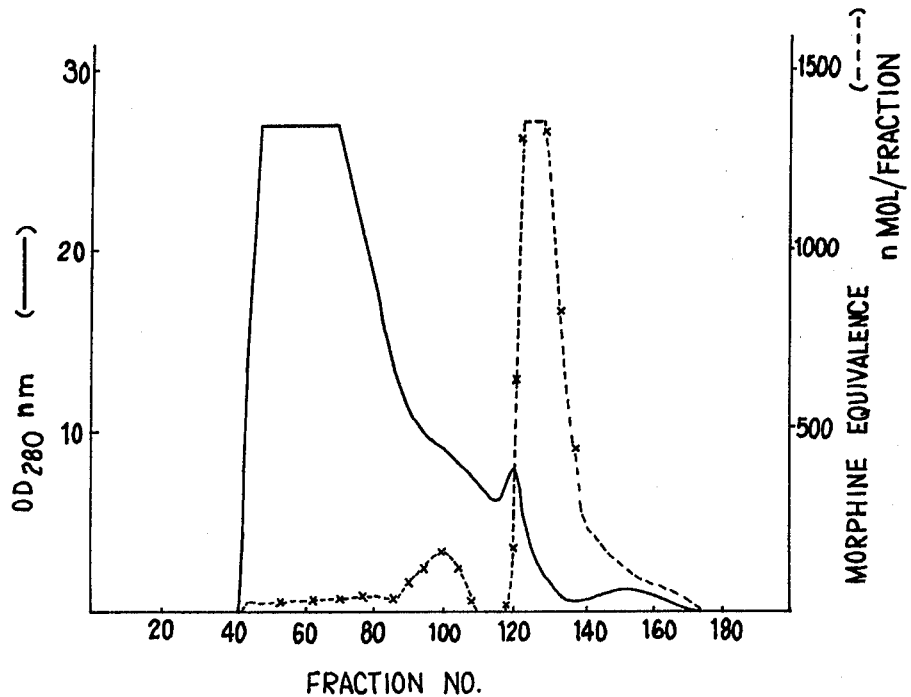
FIG. 2 refers to the Preparation Example and is a graph showing an elution profile obtained by using a Bio Gel P 6 column and an ammonium carbonate solution.
Figure 3:
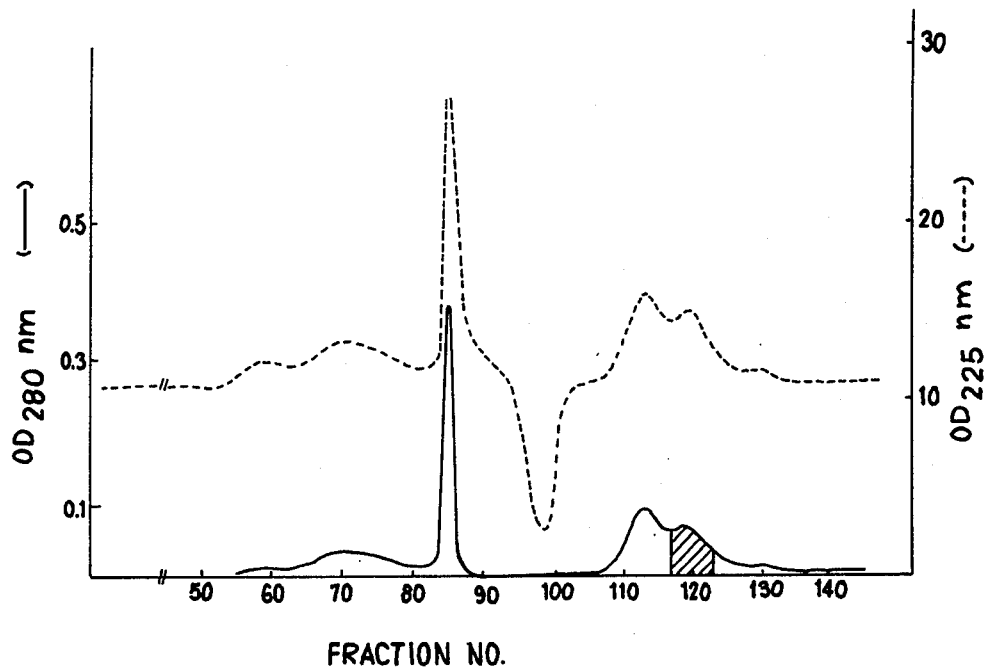
FIG. 3 refers to the Preparation Example and is a graph showing an elution profile obtained by using a Bio Gel P 6 column and an acetic acid solution.
Figure 4:
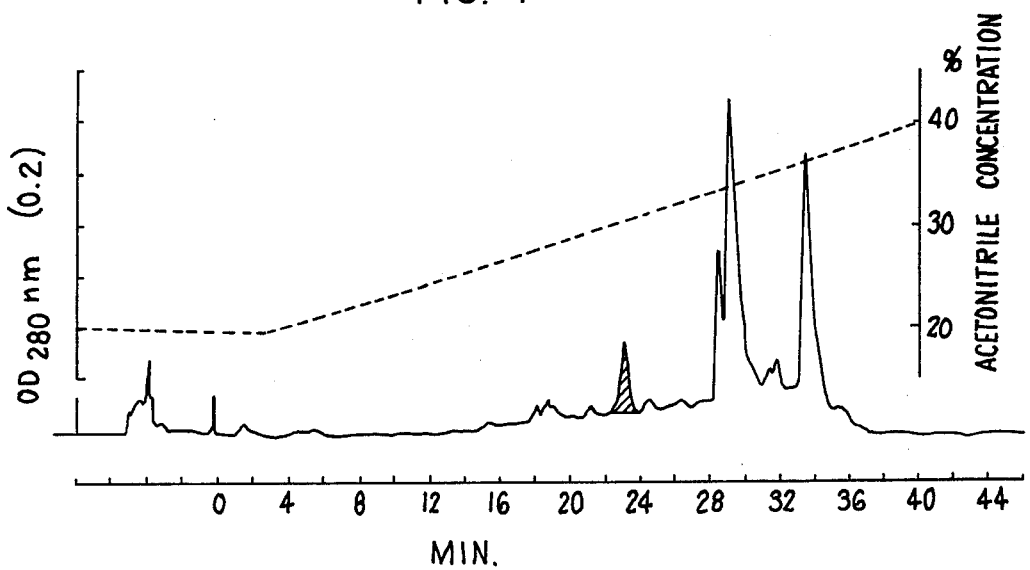
FIG. 4 refers to the Preparation Example and is a graph showing the result of reversed phase high performance liquid chromatography using a Nucleosil C 18 column.
Figure 5:
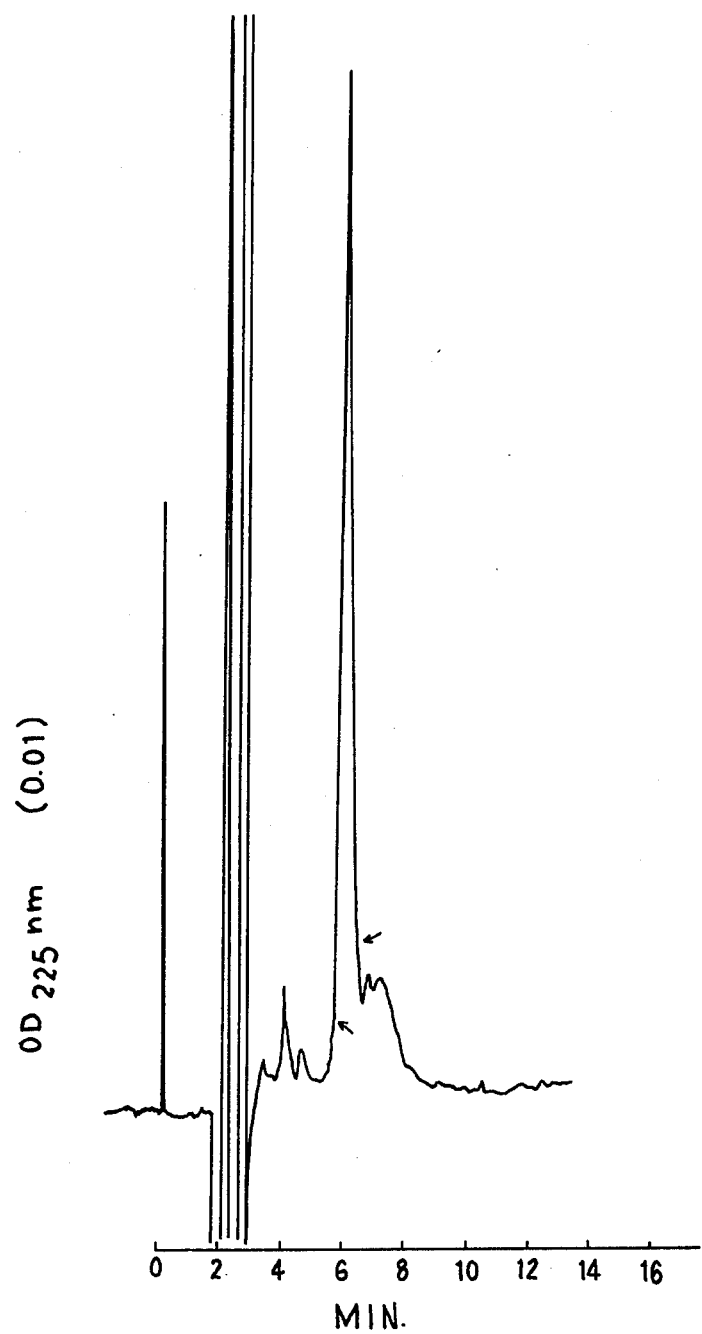
FIG. 5 refers to the Preparation Example and is the result of reversed phase high performance liquid chromatography using a Nucleosil Phenyl column.

The embodiments of the invention in which an exclusive property or privilege is claimed are defined as follows:

1. A heptadecapeptide having the following primary amino acid structure:

Tyr—Gly—Gly—Phe—Leu—Arg—Arg—Ile—Arg—Pro—Lys—Leu—Lys—Trp—Asp—Asn—Gln.

* * * * *